(12) United States Patent
Xiao et al.

(10) Patent No.: US 12,409,192 B2
(45) Date of Patent: Sep. 9, 2025

(54) TRADITIONAL CHINESE MEDICINE COMPOSITION AND USE THEREOF

(71) Applicant: JIANGSU KANION PHARMACEUTICAL CO., LTD, Jiangsu (CN)

(72) Inventors: Wei Xiao, Jiangsu (CN); Haibo Li, Jiangsu (CN); Guiping Li, Jiangsu (CN); Tuanjie Wang, Jiangsu (CN); Shasha Gu, Jiangsu (CN); Xu Li, Jiangsu (CN); Quanchang Zhang, Jiangsu (CN); Liang Cao, Jiangsu (CN); Wenjun Liu, Jiangsu (CN); Chenfeng Zhang, Jiangsu (CN); Zhenzhong Wang, Jiangsu (CN)

(73) Assignee: JIANGSU KANION PHARMACEUTICAL CO., LTD, Jiangsu (CN)

(*) Notice: Subject to any disclaimer, the term of this patent is extended or adjusted under 35 U.S.C. 154(b) by 0 days.

(21) Appl. No.: 18/715,154

(22) PCT Filed: Sep. 13, 2022

(86) PCT No.: PCT/CN2022/118405
§ 371 (c)(1),
(2) Date: May 31, 2024

(87) PCT Pub. No.: WO2023/098224
PCT Pub. Date: Jun. 8, 2023

(65) Prior Publication Data
US 2025/0017978 A1    Jan. 16, 2025

(30) Foreign Application Priority Data
Dec. 2, 2021 (CN) .......................... 202111467244.7

(51) Int. Cl.
| | | |
|---|---|---|
| A61K 36/00 | (2006.01) | |
| A61K 33/06 | (2006.01) | |
| A61K 35/32 | (2015.01) | |
| A61K 35/413 | (2015.01) | |
| A61K 36/484 | (2006.01) | |
| A61K 36/539 | (2006.01) | |
| A61K 36/708 | (2006.01) | |
| A61K 36/8966 | (2006.01) | |
| A61P 11/14 | (2006.01) | |
| A61P 29/00 | (2006.01) | |
| A61P 31/14 | (2006.01) | |

(52) U.S. Cl.
CPC ............ *A61K 35/413* (2013.01); *A61K 33/06* (2013.01); *A61K 35/32* (2013.01); *A61K 36/484* (2013.01); *A61K 36/539* (2013.01); *A61K 36/708* (2013.01); *A61K 36/8966* (2013.01); *A61P 11/14* (2018.01); *A61P 29/00* (2018.01); *A61P 31/14* (2018.01)

(58) Field of Classification Search
None
See application file for complete search history.

(56) References Cited

FOREIGN PATENT DOCUMENTS

| CN | 1251740 C | 4/2006 |
|---|---|---|
| CN | 101327294 A | 12/2008 |
| CN | 113288967 A | 8/2021 |

OTHER PUBLICATIONS

Cui et al. (2022) Front. Pharmacol. 13: 948236 (11 pages) (Year: 2022).*
Feng et al. (2023) J. Ethnopharmacology 303: 115977 (14 pages) (Year: 2023).*
Yang, Zhihui et al.; "Simultaneous Determination of 6 Components in Jinzhen Oral Solution by HPLC"; China Pharmaceuticals; vol. 26, No. 23; Dec. 5, 2017; pp. 22-25.
Cai, Mengcheng et al.; "Mechanism of Jinzhen oral liquid in treatment of coronavirus disease 2019 based on network pharmacology"; Journal of pharmaceutical Practice; vol. 38, No. 3; May 25, 2020; pp. 193-201.
Jiang, Weiwei et al.; "Research on Jinzhen oral liquid dispensing process"; (Machine translation)Machineinfo; vol. 23(Total vol. 485); Aug. 15, 2016; pp. 39-41 & 52.
Li, Haibo et al.; "Overall quality control of Jinzhen Oral Liquid based on HPLC-UVD-ELSD fingerprint and simultaneous determination of 13 main representative components"; Chinese Traditional and Herbal Drugs; vol. 51, No. 22, Nov. 30, 2020; pp. 5737-5747.
Li, Haibo et al.; "Quality control of Jinzhen Oral Liquid based on amino acids fingerprint and simultaneous determination of 29 amino acids"; Chinese Traditional and Herbal Drugs; vol. 51, No. 23; Dec. 31, 2020; pp. 5972-5979.

* cited by examiner

Primary Examiner — Russell G Fiebig
(74) Attorney, Agent, or Firm — Adam Warwick Bell; Matthew Rupert Kaser

(57) ABSTRACT

The disclosure relates to a traditional Chinese medicine composition, comprising active ingredients derived from *Cornu caprae* or *Cornu saigae tataricae*, *Radix scutellariae*, *Bulbus fritillariae ussuriensis*, *Radix glycyrrhizae*, *Radix et rhizoma rhei*, *Gypsum fibrosum*, *Calculus bovis* artifactus and Lapis Chloriti, the said active ingredients comprise in parts by weight: at least 1600 parts of amino acids; at least 120 parts of gallic acid; at least 130 parts of liquiritin; at least 20 parts of liquiritigenin; at least 400 parts of baicalin; at least 40 parts of oroxyloside; at least 120 parts of wogonoside; at least 280 parts of glycyrrhizic acid; at least 12 parts of chrysin-7-O-β-D-glucoronic acid; at least 50 parts of aloe-emodin-8-O-β-D-glucopyranoside; at least 30 parts of chrysophanol-1-O-β-D-glucopyranoside; at least 45 parts of chrysophanol-8-O-β-D-glucopyranoside; at least 260 parts of hyodeoxycholic acid; at least 150 parts of cholic acid. The traditional Chinese medicine composition in the present invention possess antipyretic, anti-inflammatory and antitussive effects.

9 Claims, No Drawings

TRADITIONAL CHINESE MEDICINE COMPOSITION AND USE THEREOF

TECHNICAL FIELD

The present invention relates to the field of traditional Chinese medicine, and in particular to a traditional Chinese medicine compound preparation and use thereof.

BACKGROUND OF THE INVENTION

Acute bronchitis (AB) is an inflammation of the bronchial mucosa caused by viral or bacterial pathogens and other infectious agents. It is a high incidence of pediatric respiratory system infections, often occurring after upper respiratory tract infections, and is commonly an early manifestation of pneumonia. AB often affects both the trachea and bronchi, hence it is also named acute tracheobronchitis. Acute bronchitis is a clinical diagnosis characterized by acute cough, with or without increased bronchial secretions. The basic pathological changes include congestion and edema of the tracheobronchial mucosa, formation of mucus plugs, increased secretion, epithelial cell damage and shedding, and infiltration of inflammatory cells. In recent years, the incidence rate of AB has increased significantly in the world, becoming a serious global public health problem. Recurrent episodes of acute bronchitis can progress to chronic bronchitis, and even further into emphysema or pulmonary heart disease, bringing heavy psychological and economic burden to patients. According to the World Health Organization, acute respiratory infections, represented by AB, are the main cause of death in children under 5 years old (excluding newborns).

Domestic and international study has shown that its basic pathological mechanism is airway inflammation. Multiple cytokines and inflammatory mediators participate in this process, with the imbalance of Th1/Th2 cell ratio being the central link in its pathogenesis, ultimately leading to airway inflammation. At present, Western medicine treatment for acute bronchitis in children is based on the principle of controlling infection, primarily using antibiotics to reduce inflammation, supplemented by antipyretic and antitussive drugs. According to reports, the most common indication for prescribing antibiotics to children in 2012 was AB (approximately 25.6%). Blind use of antibiotics can lead to serious consequences such as the emergence of drug-resistant bacteria and superinfection. In recent years, the role of traditional Chinese medicine in treating acute bronchitis in children has been increasingly valued. It offers multiple effects, including antiviral, antipyretic, and anti-inflammatory effects, and can fundamentally improve the body's immune system. It is in line with the goal of curing the disease and not only addressing the symptoms, fostering righteousness while expelling evil, and treating both the symptoms and the disease, thereby demonstrating unique advantages. Traditional Chinese medicine compound formulas are the main form of medication in traditional Chinese medicine. They are formulated by selecting and combining appropriate Chinese medicinal materials in specific proportions based on the principles of syndrome differentiation, following the sovereign, minister, assistant, and envoy principle, embodying the syndrome differentiation and treatment theory of traditional Chinese medicine. Traditional Chinese medicine compound preparations contain complex chemical components. Ensuring the safety, efficacy, and quality stability of Chinese medicinal materials and products is achieved through quality control of authentic medicinal materials at the source, ensuring the content range of active ingredients. This process facilitates the development of safe and effective Chinese medicine compound preparation for the treatment of acute bronchitis in children. The patent, application number: 02129192.6, discloses a traditional Chinese medicine composition and its preparation method for treating colds, acute and chronic bronchitis. The composition, by weight, comprises 8-12 parts of *Cornu saigae tataricae*, 30-60 parts of *Bulbus fritillariae ussuriensis*, 20-40 parts of *Radix et Rhizoma rhei*, 10-20 parts of *Radix scutellariae*, 10-20 parts of Lapis Chloriti, 15-30 parts of *Gypsum fibrosum*, 5-15 parts of *Calculus bovis* artifactus, and 20-40 parts of *Radix glycyrrhizae* as raw materials. It exhibits a good therapeutic effect on colds, acute and chronic bronchitis.

However, for traditional Chinese medicine compound formula, the raw materials mostly come from natural products. Influenced by factors such as the place of origin, growing conditions, harvesting season, and processing techniques, the quality of medicinal materials varies significantly. Even if the medicinal raw materials meet pharmacopoeial standards, different batches and origins of medicinal raw materials can still result in unstable ingredients and poor quality consistency in preparations of different batches due to differences in active ingredients. It is evident that a prescription based solely on controlling the weight of medicinal materials cannot meet the manufacturing requirements of modern traditional Chinese medicines, severely affecting the stability and controllability of clinical efficacy, as well as the repeatability and acceptance of research results. Moreover, in the complex system of traditional Chinese medicine compound formulas, the active ingredients are not clearly defined. It is unclear which main ingredients have a significant impact on efficacy and what the reasonable optimal content range is. It is necessary to reasonably control the range of different active ingredients to ensure stable quality of traditional Chinese medicine compound preparations while also ensuring their efficacy is reliable. This is a key issue constraining the development of modern traditional Chinese medicine.

BRIEF SUMMARY OF THE INVENTION

The aim of this invention is to conduct further research on the traditional Chinese medicine composition comprising eight ingredients: *Cornu caprae* or *Cornu saigae tataricae*, *Radix scutellariae*, *Bulbus fritillariae ussuriensis*, *Radix glycyrrhizae*, *Radix et Rhizoma rhei*, *Gypsum fibrosum*, *Calculus bovis* artifactus and Lapis Chloriti. By conducting component analysis and efficacy tests on traditional Chinese medicine composition formulated with medicinal materials from different origins and batches, we focus on the relationship between the main components, which exhibit significant fluctuations in content, and the results observed in efficacy tests. The aim is to identify specific active ingredients and their appropriate content ranges that can influence the pharmacological effects. This will enable us to select traditional Chinese medicine compositions with stronger activity and ensure the stability of the quality and reliability of the efficacy of traditional Chinese medicine products.

In view of this, disclosed in the present invention is a traditional Chinese medicine composition, comprising active ingredients derived from *Cornu caprae* or *Cornu saigae tataricae*, *Radix scutellariae*, *Bulbus fritillariae ussuriensis*, *Radix glycyrrhizae*, *Radix et Rhizoma rhei*, *Gypsum fibrosum*, *Calculus bovis* artifactus and Lapis Chloriti. The said active ingredients comprise, in parts by weight:

at least 1600 parts of amino acids; at least 120 parts of gallic acid; at least 130 parts of liquiritin; at least 20 parts of liquiritigenin; at least 400 parts of baicalin; at least 40 parts of oroxyloside; at least 120 parts of wogonoside; at least 280 parts of glycyrrhizic acid; at least 12 parts of chrysin-7-O-β-D-glucoronic acid; at least 50 parts of aloe-emodin-8-O-β-D-glucopyranoside; at least 30 parts of chrysophanol-1-O-β-D-glucopyranoside; at least 45 parts of chrysophanol-8-O-β-D-glucopyranoside; at least 260 parts of hyodeoxycholic acid and at least 150 parts of cholic acid.

Preferably, 1610.45-1901.21 parts of amino acids, 120.27-167.01 parts of gallic acid, 136.22-172.23 parts of liquiritin, 21.23-37.12 parts of liquiritigenin, 411.30-542.50 parts of baicalin, 40.54-55.01 parts of oroxyloside, 121.11-148.22 parts of wogonoside, 287.88-333.32 parts of glycyrrhizic acid, 12.87-24.11 parts of chrysin-7-O-β-D-glucoronic acid, 50.11-55.21 parts of aloe-emodin 8-O-β-D-glucopyranoside, 30.71-38.56 parts of chrysophanol-1-O-β-D-glucopyranoside, 45.09-57.88 parts of chrysophanol-8-O-β-D-glucopyranoside, 260.11-285.32 parts of hyodeoxycholic acid, and 151.11-191.03 parts of cholic acid.

The said pharmaceutical preparation of the composition can be in any pharmaceutically acceptable dosage forms, including any one of decoction, granule, capsule, soft capsule, pill, oral liquid, tincture, syrup, suppository, gel, spray and injection.

The preparation method thereof includes the following steps: taking 18.9 parts of *Cornu caprae* or 1.89 parts of *Cornu saigae tataricae*, 9.45 parts of *Bulbus fritillariae ussuriensis*, 6.3 parts of *Radix et Rhizoma rhei*, 3.15 parts of *Radix scutellariae*, 3.15 parts of Lapis Chloriti, 4.724 parts of *Gypsum fibrosum*, 1.89 parts of *Calculus bovis* artifactus and 6.3 parts of *Radix glycyrrhizae*; crushing the *Cornu caprae* or *Cornu saigae tataricae* into fine powder, hydrolyzing the powder with a sodium hydroxide-containing aqueous solution, filtering, and concentrating the filtrate; crushing the Lapis Chloriti and *Gympsum fibrosum* into crude powder, heating and decocting the crushed Lapis Chloriti and *Gympsum fibrosum* in water, filtering, and concentrating the filtrate; extracting the *Calculus bovis* artifactus with ethanol reflux, filtering, and concentrating the filtrate; decocting a rest of medicine in water, filtering, concentrating the filtrate and centrifuging, adding ethanol to the supernatant to precipitate, standing, taking the supernatant, filtering, recovering the ethanol under reduced pressure, concentrating, and combining the concentrated filtrate obtained above.

The present invention further provides the use of the active ingredients from the said Chinese medicine composition in the preparation of medication for antipyretic, anti-inflammatory, antitussive, and/or anti-novel coronavirus effects, such as preparing medicines for acute bronchitis.

The term "use" refers to administering the said composition to subjects exhibiting or predisposed to corresponding diseases, with the aim of imparting therapeutic effects, such as curing, alleviating, altering, influencing, improving, or preventing the said diseases, their symptoms, or predispositions. Those skilled in the art can easily determine specific effective doses based on the type of disease being treated, the route of administration, and the use of excipients. The dosage may vary due to the concurrent administration of other medications.

The present invention utilizes three animal models: dry yeast-induced fever in rats, xylene-induced ear swelling in mice, and ammonia-induced coughing in mice which confirmed that the said traditional Chinese medicine composition can significantly reduce the increase in body temperature induced by dry yeast in rats, exhibit a notable inhibitory effect on acute-phase inflammatory reactions, significantly prolong the cough latency period in mice, reduce the frequency of coughing in mice, and effectively inhibit the replication of novel coronavirus in cells, and possess significant antipyretic, anti-inflammatory, antitussive, and/or anti-novel coronavirus effects.

Moreover, the optimal content ranges of active ingredient provide the basis for quality control of the said traditional Chinese medicine composition, and this invention proposes a quality control method for the said composition, characterized by the requirement that the active ingredients should comprise: by weight, at least 1600 parts of amino acids, 120 parts of gallic acid, 130 parts of liquiritin, 20 parts of liquiritigenin, 400 parts of baicalin, 40 parts of oroxyloside, 120 parts of wogonoside, 280 parts of glycyrrhizic acid, 12 parts of chrysin-7-O-β-D-glucoronic acid, 50 parts of aloe emodin 8-O-β-D-glucopyranoside, 30 parts of chrysophanol-1-O-β-D-glucopyranoside, 45 parts of chrysophanol-8-O-β-D-glucopyranoside, 260 parts of hyodeoxycholic acid, and 150 parts of cholic acid.

Further, the said active ingredients should comprise: by weight, 1610.45-1901.21 parts of amino acids, 120.27-167.01 parts of gallic acid, 136.22-172.23 parts of liquiritin, 21.23-37.12 parts of liquiritigenin, 411.30-542.50 parts of baicalin, 40.54-55.01 parts of oroxyloside, 121.11-148.22 parts of wogonoside, 287.88-333.32 parts of glycyrrhizic acid, 12.87-24.11 parts of chrysin-7-O-β-D-glucoronic acid, 50.11-55.21 parts of aloe-emodin 8-O-β-D-glucopyranoside, 30.71-38.56 parts of chrysophanol-1-O-β-D-glucopyranoside, 45.09-57.88 parts of chrysophanol-8-O-β-D-glucopyranoside, 260.11-285.32 parts of hyodeoxycholic acid, and 151.11-191.03 parts of cholic acid.

This invention further provides a detection method for active ingredients of the said traditional Chinese medicine composition by using high performance liquid chromatography. The chromatographic conditions are as follows: chromatographic column: taking COSMOSIL-C18 with specifications of 4.6 mm×250 mm, 5.0 m as a stationary phase; mobile phase: taking methyl alcohol as mobile phase B, taking acidic water (containing 0.1% formic acid) as mobile phase A, gradient elution program is as follows: 0-15 min: 10-40% B, 15-70 min: 40-70% B, 70-90 min: 70-100% B.

DETAILED DESCRIPTION OF EMBODIMENTS

As described above, this invention aims to provide active ingredients, preparation method, use and quality control method of a traditional Chinese medicine composition. The following will provide a detailed description with test examples.

It is to be understood that similar substitutions and modifications made in accordance with the teachings of the present invention are considered to be within the scope of the invention. Such modifications and variations are apparent to those skilled in the art and are considered to be encompassed by the present invention. It will be further understood by those skilled in the art that the methods and applications described herein are exemplary only and not exhaustive, and various modifications, changes, and combinations may be made within the spirit and scope of the present invention.

Unless otherwise specified, medicines or instruments used in this invention are all common commercial products and can be purchased in the market.

Embodiment: Preparation of the Traditional Chinese Medicine Composition 15 batches of the traditional Chinese medicine compositions are prepared by combining medicinal materials from different origins and batches. Specifically, this includes: taking 94.5 g of *Cornu caprae*, 47.25 g of *Bulbus fritillariae ussuriensis*, 31.50 g of *Radix et Rhizoma rhei*, 15.75 g of Lapis Chloriti, 23.62 g of *Gypsum fibrosum*, 9.45 g of *Calculus bovis* artifactus, 31.50 g of *Radix glycyrrhizae*, *Cornu caprae* or *Cornu saigae tataricae* was crushed into fine powder, a sodium hydroxide-containing aqueous solution was used to perform reflux until nearly completely dissolved, filtering was performed, and the filtrate was concentrated; Lapis Chloriti and *Gypsum fibrosum* were smashed into crude powder, the crude powder was heated and decocted in water, filtering was performed, and the filtrate was concentrated; reflux and extraction were performed on *Calculus bovis* artifactus with ethanol, filtering was performed, and the filtrate was concentrated; the rest of medicines were decocted in water, filtering was performed, the filtrate was concentrated, and was centrifuged, liquid supernatant was precipitated by adding ethanol, standing was performed, the liquid supernatant was taken and filtered, ethanol was recycled under reduced pressure, and the filtrate was concentrated; and the concentrated filtrate obtained above was mixed. The concentrated liquor was uniformly mixed with 0.2% steviosin, water was added to make up to 1000 ml, uniformly mixing was performed, boiling was performed for 40 minutes, refrigerating was performed for not less than 48 h, filtering was performed, water was added into the filtrate until 1000 ml, a pH value of the filtrate was adjusted to be 8.0-9.0, filling and sterilizing were performed to obtain the oral liquid. The medicinal materials of *Cornu caprae* are sourced from Zhejiang, Hebei, Jiangsu, Inner Mongolia, and other regions; *Bulbus fritillariae ussuriensis* is sourced from Liaoning, Jilin, Heilongjiang, and other regions; *Radix et Rhizoma rhei* is sourced from Gansu, Qinghai, Chongqing, and other regions; *Radix scutellariae* is sourced from Shandong, Shanxi, Shanxi, Gansu, and other regions; *Radix glycyrrhizae* is sourced from Inner Mongolia, Ningxia, Gansu, Xinjiang, and other regions.

Assay

In this invention, the method for determining the content of active ingredients in traditional Chinese medicine compositions involves using an amino acid automatic analyzer and a multi-wavelength high performance liquid chromatography-vacuum ultraviolet wave-evaporative light scattering detector (HPLC-UVD-ELSD) for detection. The specific method is as follows:

Assay I: gallic acid, liquiritin, liquiritigenin, baicalin, oroxyloside, wogonoside, glycyrrhizic acid, chrysin-7-O-β-D-glucoronic acid, aloe-eModin-8-O-β-D-glucopyranoside, chrysophanol-1-O-β-D-glucopyranoside, chrysophanol-8-O-β-D-glucopyranoside, hyodeoxycholic acid, and cholic acid are determined by the high performance liquid chromatography method as specified in the "Chinese Pharmacopoeia".

Liquid chromatographic conditions and system suitability test: COSMOSIL-C18 chromatographic column (4.6 mm×250 mm, 5.0 m); mobile phase: methanol (B)-acidic water (A) (containing 0.1% formic acid), gradient elution: 0-15 min: 10-40% B, 15-70 min: 40-70% B, 70-90 min: 70-100% B; flow rate 1.0 mL/min, column temperature 35° C., ELSD flow rate 2.0 L/min, drift tube temperature 115° C., gain value 4.0.

Preparation of reference solution: (1) Preparation of single standard solutions: Precisely weigh liquiritin, glycyrrhizin acid, hyodeoxycholic acid, cholic acid, oroxyloside, chrysin-7-O-β-D-glucoronic acid, liquiritigenin, and gallic acid at 8.39 mg, 6.89 mg, 10.8 mg, 4.24 mg, 4.49 mg, 2.36 mg, 6.00 mg, and 9.40 mg respectively, place them in 5.0 mL volumetric flasks, add approximately 3.0 mL of methanol, sonicate until dissolved, and then make up to 5.0 mL with methanol. This yields reference solutions with concentrations of 1678 g/mL, 1378 μg/mL, 2160 μg/mL, 848 μg/mL, 898 μg/mL, 472 μg/mL, 1200 μg/mL, and 1880 g/mL, respectively; Precisely weigh baicalin and wogonoside at 12.08 mg and 5.54 mg, respectively, place them in 10.0 mL volumetric flasks, add approximately 7.0 mL of methanol, sonicate until dissolved, and then make up to 10.0 mL with methanol. This yields reference solutions with concentrations of 1208 μg/mL and 554 μg/mL, respectively. Precisely weigh aloe-emodin-8-O-β-D-glucopyranoside, chrysophanol-1-O-β-D-glucopyranoside, and chrysophanol-8-O-β-D-glucopyranoside at 2.08 mg, 4.51 mg, and 4.71 mg, respectively, place them in 20.0 mL volumetric flasks, add approximately 17.0 mL of methanol, sonicate until dissolved, and then make up to 20.0 mL with methanol. This yields reference solutions with concentrations of 104 μg/mL, 225.5 μg/mL, and 235.5 μg/mL, respectively. (2) Preparation of mixed reference solution: Accurately pipette different volumes of each single standard solution (1.0 mL each of liquiritin, hyodeoxycholic acid, oroxyloside, and chrysin-7-O-β-D-glucoronic acid; 0.5 mL each of gallic acid and liquiritigenin; 5.0 mL of baicalin; 4.0 mL of aloe-emodin-8-O-β-D-glucopyranoside; 2.0 mL of wogonoside, 2.5 mL of glycyrrhizic acid; 3.0 mL of chrysophanol-1-O-β-D-glucopyranoside; 1.5 mL each of cholic acid and chrysophanol-8-O-β-D-glucopyranoside) into a 25 mL volumetric flask and make up to the mark.

Preparation of test solution: Accurately pipette 1.0 mL of different batches of the Chinese medicine composition prepared in Example 1, place it in a 5.0 mL volumetric flask, add approximately 4.0 mL of distilled water, sonicate until mixed thoroughly, and then make up to 5.0 mL with distilled water. Take 1.0 mL, filter through a 0.45 m microporous membrane, and collect the subsequent filtrate.

Determination method: Accurately pipette 10 μL of each reference solution and test solution into the liquid chromatograph for measurement. Record the chromatograms and peak areas of the said 13 ingredients. Hyodeoxycholic acid and cholic acid are subjected to linear regression calculation with the natural logarithm of the mass concentration (X) as the abscissa and the natural logarithm of the peak area (Y) as the ordinate. The remaining eleven ingredients are all subjected to linear regression calculation with the mass concentration (X, g/mL) as the abscissa and the peak area (Y) as the ordinate for quantitative analysis. See Table 1 for specific content result of each batch.

TABLE 1

Determination results of the contents of amino acids, gallic acid, liquiritin, liquiritigenin, baicalin, oroxyloside, wogonoside, glycyrrhizic acid, chrysin-7-O-β-D-glucoronic acid, aloe-emodin-8-O-β-D-glucopyranoside, chrysophanol-1-O-β-D-glucopyranoside, chrysophanol-8-O-β-D-glucopyranoside, hyodeoxycholic acid, and cholic acid in 15 batches of the traditional Chinese medicine composition (μg/mL)

| batch name | gallic acid | liquiritin | aloe-emodin-8-O-β-D-glucopyranoside | liquiritigenin | baicalin | chrysin-7-O-β-D-glucoronic acid | oroxyloside |
|---|---|---|---|---|---|---|---|
| A | 49.11 | 55.11 | 39.99 | 22.88 | 598.68 | 16.63 | 59.11 |
| B | 128.52 | 136.22 | 52.11 | 37.12 | 542.50 | 24.11 | 48.76 |
| C | 167.01 | 141.32 | 50.11 | 21.32 | 489.25 | 20.11 | 53.65 |
| D | 120.27 | 144.96 | 55.21 | 25.01 | 465.65 | 12.87 | 55.01 |
| E | 170.52 | 148.14 | 35.09 | 39.01 | 582.11 | 22.66 | 70.25 |
| F | 130.33 | 86.98 | 60.01 | 42.56 | 740.12 | 28.22 | 85.60 |
| G | 92.01 | 104.22 | 39.11 | 19.11 | 700.11 | 21.01 | 77.61 |
| H | 105.65 | 110.89 | 34.65 | 39.65 | 845.00 | 36.01 | 97.12 |
| I | 133.01 | 151.03 | 53.63 | 32.02 | 500.88 | 16.98 | 40.54 |
| J | 155.11 | 89.01 | 47.21 | 20.01 | 547.09 | 36.88 | 81.02 |
| K | 79.08 | 77.96 | 33.15 | 24.91 | 723.98 | 14.55 | 78.93 |
| L | 80.02 | 85.01 | 44.25 | 22.01 | 721.01 | 15.08 | 77.02 |
| M | 111.96 | 101.21 | 33.66 | 30.61 | 611.11 | 13.56 | 75.22 |
| N | 150.01 | 172.23 | 54.44 | 35.55 | 411.30 | 18.55 | 49.46 |
| O | 151.12 | 78.13 | 39.12 | 34.12 | 824.12 | 10.99 | 77.12 |

| batch name | wogonoside | chrysophanol-1-O-β-D-glucopyranoside | chrysophanol-8-O-β-D-glucopyranoside | glycyrrhizic acid | hyodeoxycholic acid | cholic acid |
|---|---|---|---|---|---|---|
| A | 164.14 | 15.98 | 39.81 | 277.45 | 154.12 | 121.12 |
| B | 121.11 | 38.56 | 52.01 | 333.32 | 270.23 | 175.65 |
| C | 131.15 | 36.33 | 49.11 | 312.05 | 268.11 | 151.11 |
| D | 129.96 | 31.87 | 57.88 | 300.21 | 285.32 | 165.03 |
| E | 148.22 | 19.10 | 20.12 | 244.12 | 200.12 | 135.52 |
| F | 171.01 | 18.01 | 20.63 | 298.11 | 260.66 | 100.33 |
| G | 160.11 | 10.96 | 19.11 | 230.01 | 201.00 | 131.11 |
| H | 202.12 | 11.19 | 18.88 | 229.12 | 214.12 | 115.98 |
| I | 140.66 | 31.25 | 45.09 | 287.88 | 265.66 | 191.03 |
| J | 130.12 | 19.12 | 27.09 | 269.04 | 228.01 | 108.01 |
| K | 166.01 | 13.56 | 20.45 | 239.01 | 211.23 | 105.11 |
| L | 266.01 | 22.10 | 22.63 | 235.23 | 210.56 | 116.03 |
| M | 160.42 | 11.45 | 21.01 | 220.16 | 185.69 | 99.10 |
| N | 148.22 | 30.71 | 49.98 | 292.12 | 260.11 | 170.02 |
| O | 135.12 | 16.23 | 28.24 | 256.65 | 190.74 | 115.54 |

Assay II: Amino Acids

Liquid chromatographic conditions and system suitability test: Chromatographic column: Hitachi 855-4507 ion exchange chromatographic column; Mobile phase: citric acid buffer solution; Detector: fluorescence detector; Elution pump flow rate: 0.35 mL/min; Derivative pump flow rate: 0.30 mL/min; Column temperature: 135° C. (Programmed temperature ramp); Detection wavelengths: 570 nm, 440 nm; Injection volume: 20 L; Analysis duration: 148 min.

Preparation of reference solution: Accurately weigh 36.535 mg of L-glutamine reference standard and place it in a 100 mL volumetric flask, add an appropriate amount of water, sonicate for 5 minutes to dissolve, and dilute to the mark with water to obtain a 2.5 mol/mL L-glutamine reference stock solution. Accurately pipette 400 μL each of amino acid mixed standard solution B, AN-II type, L-aspartic acid standard solution, and L-glutamine reference standard stock solution into a 10 mL volumetric flask, add an appropriate amount of 0.02 mol/L hydrochloric acid for dilution, sonicate for 5 minutes to mix, and dilute to the mark with 0.02 mol/L hydrochloric acid to obtain a 100 nmol/mL amino acid standard solution, which is referred to as standard solution 1.

Preparation of Standard Curve Solution:

Accurately pipette 6 mL of standard solution 1 into a 10 mL volumetric flask, dilute to 10 mL with 0.02 mol/L hydrochloric acid to obtain a standard solution 2 containing 60 nmol/mL of amino acids.

Accurately pipette 5 mL of standard solution 2 into a 10 mL volumetric flask, dilute to 10 mL with 0.02 mol/L hydrochloric acid to obtain a standard solution 3 containing 30 nmol/mL of amino acids.

Accurately pipette 5 mL of standard solution 3 into a 10 mL volumetric flask, dilute to 10 mL with 0.02 mol/L hydrochloric acid to obtain a standard solution 4 containing 15 nmol/mL of amino acids.

Accurately pipette 2 mL of standard solution 1 into a 10 mL volumetric flask, dilute to 10 mL with 0.02 mol/L hydrochloric acid to obtain a standard solution 5 containing 20 nmol/mL of amino acids.

Accurately pipette 5 mL of standard solution 1 into a 100 mL volumetric flask, dilute to 100 mL with 0.02 mol/L hydrochloric acid to obtain a standard solution 6 containing 5 nmol/mL of amino acids.

Preparation of test solution: According to the requirements of the amino acid automatic analyzer for sample preparation, perform sample pretreatment. Take 2 mL of the finished product, add an equal volume of 5% salicylic acid, place in a −4° C. refrigerator for 24 hours, centrifuge at 12000 rpm for 10 minutes, take the supernatant, add an equal volume of 0.02 mol/mL HCl for dilution.

Determination method: Prepare a series of standard solutions with different concentrations, inject them sequentially according to the analysis conditions of liquid chromatography, record and analyze the chromatographic peak areas of the quantitative ingredients. Use the mass concentration (g/mL) as the abscissa and the peak area as the ordinate, perform linear regression calculation for the quantitative amino acid ingredients, and obtain the regression equation, correlation coefficient, and linear range for each quantitative amino acid. See Table 2 for content result of each batch.

TABLE 2

Determination results of the total amino acids' content in 15 batches of the traditional Chinese medicine composition (μg/mL)

| Batch name | Total amino acids (μg/mL) |
| --- | --- |
| A | 675.21 |
| B | 1682.11 |
| C | 1610.45 |
| D | 1701.23 |
| E | 777.66 |
| F | 870.10 |
| G | 991.36 |
| H | 799.89 |
| I | 1719.10 |
| J | 654.23 |
| K | 1345.12 |
| L | 1444.96 |
| M | 1141.20 |
| N | 1901.21 |
| O | 931.12 |

Efficacy Test Example

Experimental study of 15 batches of the traditional Chinese medicine composition on fever induced by dry yeast in rats, ear swelling induced by xylene in mice, and cough induced by ammonia in mice.

1. Experimental Materials
1.1 Tested Medicine and Reagents
A-O, 15 batches of the traditional Chinese medicine composition, made by Jiangsu Kanion Pharmaceutical Co., Ltd; Enteric-coated aspirin tablets, specification of 100 mg/tablet; Promethazine hydrochloride granules, specification of 1.5 mg/sachet; Dry yeast, specification of 15 g/sachet; Xylene, ammonia solution.

1.2 Experimental Instrument
15-D03A thermometer, BS224S electronic analytical balance, Mouse ear puncher, YLS-8A multi-functional cough and asthma meter.
1.3 Experimental Animals
SD rats of SPF grade, male, weighing 180-220 g; KM mice of SPF grade, male, weighing 18-22 g; ICR mice of SPF grade, half male and half female, weighing 18-22 g.
2. Methods
2.1 Effect of Different Batches of the Composition on Fever Induced by Dry Yeast in Rats
(1) Experimental Method
Male SD rats, weighing 180-220 g were fed adaptively for 1 week, with the environmental temperature maintained at 20-25° C. The rectal temperature of the rats was measured once daily at 10:00 am for two consecutive days to acclimate them to this procedure. The average of the two temperature measurements was taken as the baseline temperature. Rats with a temperature range of 37.0-38.6° C. and a fluctuation <0.5° C. were selected for the experiment. Each rat was subcutaneously injected with 10 ml/kg of a 20% suspension of dry yeast to induce fever. (Preparation method: 120 g of dry yeast was weighed and placed in a mortar, gradually adding distilled water to grind into a uniform suspension, and then adjusted to a volume of 600 mL, prepare this solution fresh.) Six hours after injecting the yeast suspension, the body temperature of the rats was measured. One hundred and seventy rats with a temperature increase ranging from 1.0 to 2.2 degrees Celsius were selected and randomly divided into 17 groups based on their temperatures. These groups were as follows: (1) Model group: administered distilled water, (2) Traditional Chinese medicine composition groups A-O: dosage of 3.34 g crude drugs/kg, (3) Positive control group: administered aspirin suspension, dosage of 0.20 g/kg. Each group was orally gavaged with the corresponding solvent or drug, and rectal temperature was measured at 1 h, 2 h, 3 h, 4 h, and 5 h after administration to calculate the temperature difference from baseline.
(2) Results
Compared with the model group, each treatment group could reduce the elevated body temperature induced by dry yeast in rats at 2 h, 3 h, 4 h, and 5 h after administration. Among them, the differences were more significant in the groups treated with the traditional Chinese medicine compositions of B, C, D, H, I, J, and N compared to the model group. See Table 3 for detailed results.

TABLE 3

Effects of different Batches of the traditional Chinese medicine composition on Dry yeast-induced Fever in Rats ($\overline{X} \pm SD$, n = 10)

| Group name | Temperature rise degrees caused by fever (ΔT) | Temperature rise degrees at different time points after administration of medication (ΔT) | | | | |
| --- | --- | --- | --- | --- | --- | --- |
| | | 1 h | 2 h | 3 h | 4 h | 5 h |
| Model group | 1.65 ± 0.36 | 2.32 ± 0.27 | 2.25 ± 0.22 | 2.13 ± 0.25 | 1.98 ± 0.28 | 1.50 ± 0.24 |
| A | 1.65 ± 0.32 | 2.20 ± 0.21 | 1.95 ± 0.20** | 1.84 ± 0.32* | 1.69 ± 0.41 | 1.35 ± 0.31 |
| B | 1.61 ± 0.31 | 2.25 ± 0.26 | 1.81 ± 0.31** | 1.65 ± 0.36** | 1.15 ± 0.43** | 1.08 ± 0.34** |
| C | 1.62 ± 0.39 | 2.30 ± 0.33 | 1.83 ± 0.33** | 1.66 ± 0.22** | 1.45 ± 0.38** | 1.06 ± 0.27** |
| D | 1.61 ± 0.30 | 2.13 ± 0.31 | 1.81 ± 0.36** | 1.74 ± 0.29** | 1.40 ± 0.49** | 1.06 ± 0.40** |
| E | 1.65 ± 0.31 | 2.14 ± 0.41 | 2.20 ± 0.30 | 1.94 ± 0.47 | 1.65 ± 0.37* | 1.31 ± 0.25 |
| F | 1.64 ± 0.35 | 2.21 ± 0.24 | 1.97 ± 0.26* | 1.99 ± 0.32 | 1.80 ± 0.41 | 1.40 ± 0.31 |
| G | 1.60 ± 0.33 | 2.25 ± 0.26 | 2.08 ± 0.30 | 1.99 ± 0.34 | 1.15 ± 0.43** | 1.30 ± 0.31 |
| H | 1.63 ± 0.41 | 2.26 ± 0.34 | 1.82 ± 0.35** | 1.66 ± 0.22** | 1.56 ± 0.51* | 1.06 ± 0.27** |

TABLE 3-continued

Effects of different Batches of the traditional Chinese medicine composition on Dry yeast-induced Fever in Rats ($\overline{X} \pm SD$, n = 10)

| Group name | Temperature rise degrees caused by fever ($\Delta T$) | Temperature rise degrees at different time points after administration of medication ($\Delta T$) | | | | |
|---|---|---|---|---|---|---|
| | | 1 h | 2 h | 3 h | 4 h | 5 h |
| I | 1.61 ± 0.34 | 2.23 ± 0.29 | 1.83 ± 0.11** | 1.72 ± 0.30** | 1.40 ± 0.49** | 1.06 ± 0.35** |
| J | 1.65 ± 0.31 | 2.15 ± 0.43 | 1.81 ± 0.30** | 1.63 ± 0.41** | 1.17 ± 0.44** | 1.09 ± 0.35** |
| K | 1.64 ± 0.34 | 2.11 ± 0.43 | 2.18 ± 0.23 | 1.88 ± 0.25* | 1.63 ± 0.47 | 1.35 ± 0.31 |
| L | 1.64 ± 0.44 | 2.29 ± 0.24 | 2.20 ± 0.25 | 1.87 ± 0.22* | 1.68 ± 0.42 | 1.28 ± 0.34 |
| M | 1.65 ± 0.35 | 2.30 ± 0.25 | 2.22 ± 0.22 | 1.83 ± 0.34* | 1.69 ± 0.42 | 1.35 ± 0.35 |
| N | 1.62 ± 0.33 | 2.23 ± 0.31 | 1.81 ± 0.31** | 1.65 ± 0.30** | 1.40 ± 0.49** | 1.06 ± 0.33** |
| O | 1.65 ± 0.31 | 2.14 ± 0.42 | 1.98 ± 0.31* | 1.94 ± 0.47 | 1.65 ± 0.44 | 1.39 ± 0.35 |
| Positive control group | 1.60 ± 0.26 | 0.40 ± 0.24** | 0.34 ± 0.37** | 0.27 ± 0.28** | 0.22 ± 0.23** | 0.22 ± 0.24** |

Compared with the model group:
*P < 0.05,
**P < 0.01.

2.2 Effects of Different Batches of the Traditional Chinese Medicine Composition on Xylene-Induced Ear Swelling in Mice Experimental Method Male KM rats, weighing 180-220 g were fed adaptively for 4 days, with the environmental temperature maintained at 20-25° C. They were randomly divided into 17 groups, each consisting of 10 mice: (1) Model group: administered distilled water, (2) Traditional Chinese medicine groups A-O: dosage at 4.83 g of crude drugs/kg, and (3) Positive control group: administered aspirin suspension at a dosage of 0.20 g/kg. Mice in each group were orally gavaged once daily for 5 consecutive days. One hour after the final administration, 0.03 ml of xylene was applied to both sides of the right ear of each mouse, while the left ear served as a control. One hour later, the mice were euthanized by cervical dislocation, and 8 mm ear punches were taken from the same location on both ears of each mouse. The ear punches were weighed precisely, and the difference in weight between the right and left ears was calculated as the degree of swelling.

(2) Results

Compared to the model group, all treatment groups were able to suppress xylene-induced ear swelling in mice. Among them, significant differences were observed in the groups treated with the traditional Chinese medicine compositions of B, C, D, H, I, M, N, and O compared to the model group. See Table 4 for detailed results."

TABLE 4

Effects of different batches of the traditional Chinese medicine composition on xylene-induced ear swelling in mice ($\overline{X} \pm SD$, n = 10)

| Group name | Degree of swelling(g) |
|---|---|
| Model group | 0.0165 ± 0.0062 |
| A | 0.0113 ± 0.0109 |
| B | 0.0082 ± 0.0076** |
| C | 0.0085 ± 0.0055** |
| D | 0.0084 ± 0.0042** |
| E | 0.0121 ± 0.0089 |
| F | 0.0136 ± 0.0042 |
| G | 0.0124 ± 0.0109 |
| H | 0.0103 ± 0.0061* |
| I | 0.0087 ± 0.0055** |
| J | 0.0115 ± 0.0043 |
| K | 0.0133 ± 0.0081 |
| L | 0.0109 ± 0.0054 |
| M | 0.0101 ± 0.0061* |
| N | 0.0085 ± 0.0067** |
| O | 0.0084 ± 0.0049** |
| Positive control group (Aspirin) | 0.0076 ± 0.0042** |

Compared with model group:
*P < 0.05,
**P < 0.01.

2.3 Effects of Different Batches of the Traditional Chinese Medicine Composition on Ammonia Solution-Induced Cough in Mice (1) Experimental Method ICR mice weighing between 18-22 g, half male and half female, conducting pre-screening, qualified mice were fed for 3 days, (mice with a latent period of less than 1 minute and experiencing typical coughing at least 3 times within 1 minute are classified as 'coughing' sensitive animals. Otherwise, they are classified as 'non-coughing' and eliminated). Then, randomly divide them into 17 groups: (1) Model group: administered distilled water; (2) Traditional Chinese medicine composition groups A-O: dosage of 4.83 g of crude drug/kg; (3) Positive control group: given a suspension of promethazine hydrochloride, dosage of 1.79 mg/kg. Mice in each group are orally administered once daily for 5 consecutive days. One hour after the final administration, mice are placed in a glass chamber of a multi-function cough and asthma meter, and 25-28% ammonia solution is sprayed into the chamber for 3 seconds. Subsequently, observe and record the cough latency period and the number of coughs within 3 minutes for each mouse. The criteria for coughing include: abdominal muscle contraction, simultaneous mouth opening, and sometimes coughing sounds.

(2) Results:

Compared to the model group, all treatment groups showed significant prolongation of the cough latency period and/or significant reduction in the number of coughs in mice. Among them, the compositions of B, C, D, F, I, K, and N exhibited significant differences compared to the model group. See Table 5 for detailed results.

TABLE 5

Effects of different batches of the traditional Chinese medicine composition on ammonia-induced cough in mice ($\overline{X} \pm SD$, n = 10)

| Group name | Cough latency period (s) | Number of coughs (times) |
|---|---|---|
| Model group | 39.76 ± 7.21 | 17.90 ± 2.96 |
| A | 40.13 ± 10.99 | 14.60 ± 5.72 |
| B | 49.10 ± 7.09* | 10.00 ± 3.30** |
| C | 48.11 ± 8.41* | 11.70 ± 2.83** |
| D | 49.34 ± 7.54* | 10.70 ± 3.71** |
| E | 40.54 ± 8.41 | 14.90 ± 4.16 |
| F | 43.76 ± 8.21 | 12.90 ± 4.96* |
| G | 46.13 ± 10.99 | 15.40 ± 5.72 |
| H | 47.10 ± 9.09 | 14.00 ± 5.20 |
| I | 49.51 ± 6.47** | 10.10 ± 2.83** |
| J | 45.34 ± 7.54 | 14.60 ± 3.91 |
| K | 50.54 ± 7.61** | 9.90 ± 4.56** |
| L | 41.34 ± 7.54 | 13.40 ± 5.61 |
| M | 40.54 ± 8.41 | 15.90 ± 4.66 |
| N | 49.10 ± 7.09* | 10.00 ± 3.30** |
| O | 46.11 ± 8.94 | 15.70 ± 2.83 |
| Positive control group | 50.37 ± 8.88* | 9.70 ± 4.20** |

Compared with model group:
*$P < 0.05$,
**$P < 0.01$.

2.4 the Anti-Novel Coronavirus Efficacy of Different Batches of the Traditional Chinese Medicine Composition (1) Experimental Materials Tested Medicines: Different Batches of the Composition (A-O)

VeroE6 cell: Stored in Pathogen Center, Institute of Medical Laboratory Animal, Chinese Academy of Medical Sciences.

2019-nCoV virus: with titer of 105TCID50/ml, stored at −80 DEG (° C.) in Pathogen Center, Institute of Medical Laboratory Animal, Chinese Academy of Medical Sciences. Viral titer used is 100 TCID50.

(2) Experimental Method

In a sterile 96-well culture plate, 200 ul of a Vero E6 cell with a concentrated of 5×104 cell/ml was added into each well, and was cultured with 5% CO2 for 24 hours at 37 DEG (° C.); a test medicine was diluted to have three concentrations: (1:10000, 1:20000, 1:50000), five wells for each concentration, 100 ul in each well; an equal volume of 100 TCID50 virus was added into each cell, and was incubated for 1 h; 1 h later, cell culture fluid in the 96-well culture plate was discarded, and the medicine mixed liquor was added; cell control, blank control (solvent control) and virus control (negative control) were set at the same time; the cell was incubated in an incubator with 5% CO2 at 37 DEG (° C.) for 4-5 days. Cytopathic effect (CPE) was observed under an optical microscope, complete cell cytopathy was recorded as "++++", 75% cell cytopathy was recorded as "+++", 50% cell cytopathy was recorded as "++", 25% cell cytopathy was recorded as "+", and no cell cytopathy was recorded as "−".

(3) Experimental Conditions

The Experimental operations were all completed in a BSL-3 Laboratory.

(4) Result Judgement when the cell had no CPE, the concentration could effectively inhibit the virus; and when the cell had CPE, the concentration was ineffective.

(5) Results

The medicine group was set with three concentrations at which 2019-nCoV replication in the cell could be effectively inhibited. See Table 6 for detailed results.

TABLE 6

Anti-2019-nCoV effect of different batches of the traditional Chinese medicine composition

| Names of the tested medicine | Concentration | Results |
|---|---|---|
| A | 1:10000 | + |
|   | 1:20000 |   |
|   | 1:50000 |   |
| B | 1:10000 | − |
|   | 1:20000 |   |
|   | 1:50000 |   |
| C | 1:10000 | − |
|   | 1:20000 |   |
|   | 1:50000 |   |
| D | 1:10000 | − |
|   | 1:20000 |   |
|   | 1:50000 |   |
| E | 1:10000 | + |
|   | 1:20000 |   |
|   | 1:50000 |   |
| F | 1:10000 | + |
|   | 1:20000 |   |
|   | 1:50000 |   |
| G | 1:10000 | + |
|   | 1:20000 |   |
|   | 1:50000 |   |
| H | 1:10000 | + |
|   | 1:20000 |   |
|   | 1:50000 |   |
| I | 1:10000 | − |
|   | 1:20000 |   |
|   | 1:50000 |   |
| J | 1:10000 | + |
|   | 1:20000 |   |
|   | 1:50000 |   |
| K | 1:10000 | + |
|   | 1:20000 |   |
|   | 1:50000 |   |
| L | 1:10000 | + |
|   | 1:20000 |   |
|   | 1:50000 |   |
| M | 1:10000 | + |
|   | 1:20000 |   |
|   | 1:50000 |   |
| N | 1:10000 | − |
|   | 1:20000 |   |
|   | 1:50000 |   |
| O | 1:10000 | + |
|   | 1:20000 |   |
|   | 1:50000 |   |
| Negative control |   | ++++ |

(6) Conclusion

Based on a cell-level screening result, the composition of B, C, D, I, N could inhibit 2019-nCoV replication in the cell at 1:10000, 1:20000, 1:50000 dilution concentration, indicating good in-vitro anti-2019-nCoV activity.

3. Conclusion

In three animal models-rat fever induced by dry yeast, mouse ear swelling induced by xylene, and mouse cough induced by ammonia, as well as in the anti-novel coronavirus study-different batches of the traditional Chinese medicine composition all showed significant reductions in rat body temperature elevation caused by dry yeast, exhibited notable inhibitory effects on acute inflammatory reaction, significantly prolonged the cough latency period in mice, reduced the frequency of coughing in mice, and effectively inhibited the replication of the novel coronavirus in cells. Overall, the compositions of B, C, D, I, and N demonstrated more significant antipyretic, anti-inflammatory, and antitussive effects as well as anti-novel coronavirus effects.

Based on the content of specific ingredients in B, C, D, I and N, optimal ranges of contents can be summarized as follows: 1610.45-1901.21 parts of amino acids, 120.27-167.01 parts of gallic acid, 136.22-172.23 parts of liquiritin, 21.23-37.12 parts of liquiritigenin, 411.30-542.50 parts of baicalin, 40.54-55.01 parts of oroxyloside, 121.11-148.22 parts of wogonoside, 287.88-333.32 parts of glycyrrhizic acid, 12.87-24.11 parts of chrysin-7-O-β-D-glucoronic acid, 50.11-55.21 parts of aloe-emodin 8-O-β-D-glucopyranoside, 30.71-38.56 parts of chrysophanol-1-O-β-D-glucopyranoside, 45.09-57.88 parts of chrysophanol-8-O-β-D-glucopyranoside, 260.11-285.32 parts of hyodeoxycholic acid, 151.11-191.03 parts of cholic acid.

Verification of Content Ranges of the Main Ingredients

A total of 7 batches of traditional Chinese medicine compositions were prepared by combining medicinal materials from different origins and batches. After testing, the content of each active ingredient is shown in Table 7 and Table 8.

TABLE 7

Determination results of the following components' content: amino acids, gallic acid, liquiritin, liquiritigenin, baicalin, oroxyloside, wogonoside, glycyrrhizic acid, chrysin-7-O-β-D-glucoronic acid, aloe-emodin-8-O-β-D-glucopyranoside, chrysophanol-1-O-β-D-glucopyranoside, chrysophanol-8-O-β-D-glucopyranoside, hyodeoxycholic acid, cholic acid (μg/mL) in 7 batches

| batch numer | gallic acid | liquiritin | aloe-emodin-8-O-β-D-glucopyranoside | liquiritigenin | baicalin | chrysin-7-O-β-D-glucoronic acid | oroxyloside |
|---|---|---|---|---|---|---|---|
| P | 56.37 | 68.83 | 17.79 | 22.01 | 301.26 | 10.36 | 72.64 |
| Q | 100.14 | 110.77 | 33.33 | 39.12 | 809.14 | 33.09 | 98.49 |
| R | 125.28 | 170.02 | 50.23 | 36.91 | 541.11 | 22.56 | 51.26 |
| S | 139.26 | 138.63 | 55.20 | 31.25 | 501.19 | 19.36 | 49.12 |
| T | 77.09 | 89.03 | 31.16 | 29.99 | 822.33 | 32.03 | 70.12 |
| U | 159.11 | 139.65 | 51.23 | 26.12 | 465.13 | 20.13 | 48.12 |
| V | 32.12 | 183.12 | 21.46 | 11.30 | 529.96 | 18.36 | 33.64 |

| batch numer | wogonoside | chrysophanol-1-O-β-D-glucopyranoside | chrysophanol-8-O-β-D-glucopyranoside | glycyrrhizic acid | hyodeoxycholic acid | cholic acid |
|---|---|---|---|---|---|---|
| P | 100.32 | 10.32 | 12.34 | 123.01 | 150.36 | 106.32 |
| Q | 2.7.13 | 11.11 | 20.29 | 242.90 | 238.88 | 107.16 |
| R | 139.96 | 35.12 | 52.01 | 290.36 | 277.15 | 189.06 |
| S | 131.26 | 34.56 | 48.36 | 299.99 | 268.11 | 164.12 |
| T | 180.20 | 18.11 | 22.00 | 260.12 | 231.03 | 110.89 |
| U | 126.69 | 32.65 | 56.10 | 330.44 | 282.11 | 160.01 |
| V | 164.06 | 8.21 | 8.63 | 102.94 | 87.38 | 54.63 |

TABLE 8

Determination results of the total amino acids' content in 7 batches

| Batch name | Total amino acids (μg/mL) |
|---|---|
| P | 563.77 |
| Q | 1333.02 |
| R | 1701.55 |
| S | 1801.99 |
| T | 1099.89 |
| U | 1888.80 |
| V | 1555.98 |

Efficacy Verification Example

1. Experimental Method 1.1 Methods 2.1 Effect of Different Batches of the Traditional Chinese Medicine Composition on Fever Induced by Dry Yeast in Rats (1) Experimental Method Male SD rats, weighing 180-220 g were fed adaptively for 1 week, with the environmental temperature maintained at 20-25° C. The rectal temperature of the rats was measured once daily at 10:00 am for two consecutive days to acclimate them to this procedure. The average of the two temperature measurements was taken as the baseline temperature. Rats with a temperature range of 37.0-38.6° C. and a fluctuation <0.5° C. were selected for the experiment. Each rat was subcutaneously injected with 10 ml/kg of a 20% suspension of dry yeast to induce fever. (Preparation method: 120 g of dry yeast was weighed and placed in a mortar, gradually adding distilled water to grind into a uniform suspension, and then adjusted to a volume of 600 mL, prepare this solution fresh.) Six hours after injecting the yeast suspension, the body temperature of the rats was measured. Ninety rats with a temperature increase ranging from 1.0 to 2.2 degrees Celsius were selected and randomly divided into 9 groups based on their temperatures. These groups were as follows: (1) Model group: administered distilled water, (2) 7 batches of traditional Chinese medicine groups P-V: dosage of 3.34 g crude drugs/kg, (3) Positive control group: administered aspirin suspension, dosage of 0.20 g/kg. Each group was orally gavaged with the corresponding solvent or drug, and rectal temperature was measured at 1 h, 2 h, 3 h, 4 h, and 5 h after administration to calculate the temperature difference from baseline.

(2) Results

Compared with the model group, each treatment group could reduce the elevated body temperature induced by dry yeast in rats at 2 h, 3 h, 4 h, and 5 h after administration. Among them, the differences were more significant in the groups treated with the traditional Chinese medicine composition R, S, and U compared to the model group. Refer to Table 9 for the results.

TABLE 9

Effects of different batches of the traditional Chinese medicine composition on Dry yeast-induced Fever in Rats ($\overline{X} \pm SD$, n = 10)

| Group name | Degrees of temperature rise caused by fever ($\Delta T$) | Degrees of temperature rise at different time points after administration of medication ($\Delta T$) | | | | |
|---|---|---|---|---|---|---|
| | | 1 h | 2 h | 3 h | 4 h | 5 h |
| Model group | 1.65 ± 0.35 | 2.34 ± 0.22 | 2.27 ± 0.31 | 2.14 ± 0.32 | 1.98 ± 0.28 | 1.51 ± 0.19 |
| P | 1.62 ± 0.31 | 2.25 ± 0.27 | 2.20 ± 0.29 | 1.88 ± 0.27 | 1.63 ± 0.31* | 1.24 ± 0.30* |
| Q | 1.64 ± 0.42 | 2.31 ± 0.26 | 2.20 ± 0.26 | 1.84 ± 0.39* | 1.63 ± 0.38* | 1.31 ± 0.31 |
| R | 1.62 ± 0.28 | 2.13 ± 0.32 | 1.81 ± 0.42** | 1.71 ± 0.25** | 1.36 ± 0.43** | 1.06 ± 0.32** |
| S | 1.65 ± 0.30 | 2.14 ± 0.41 | 1.79 ± 0.30** | 1.63 ± 0.48** | 1.16 ± 0.45** | 0.96 ± 0.29** |
| T | 1.64 ± 0.40 | 2.30 ± 0.34 | 2.15 ± 0.38 | 1.98 ± 0.22 | 1.57 ± 0.39* | 1.30 ± 0.30 |
| U | 1.63 ± 0.35 | 2.19 ± 0.58 | 1.86 ± 0.44** | 1.77 ± 0.26** | 1.40 ± 0.40** | 1.15 ± 0.35** |
| V | 1.64 ± 0.34 | 2.26 ± 0.34 | 2.19 ± 0.31 | 1.99 ± 0.25 | 1.47 ± 0.36** | 1.20 ± 0.30* |
| Positive control group | 1.62 ± 0.27 | 0.42 ± 0.34** | 0.42 ± 0.31** | 0.34 ± 0.31** | 0.23 ± 0.30** | 0.17 ± 0.13** |

Compared with the model group:
*$P < 0.05$,
**$P < 0.01$.

1.2 Effects of Different Batches of the Traditional Chinese Medicine Composition on Xylene-Induced Ear Swelling in Mice Experimental Method Male KM rats, weighing 180-220 g were fed adaptively for 4 days, with the environmental temperature maintained at 20-25° C. They were randomly divided into 9 groups, each consisting of 10 mice: (1) Model group: administered distilled water, (2) Traditional Chinese medicine groups P-V: dosage at 4.83 g of crude drugs/kg, and (3) Positive control group: administered aspirin suspension at a dosage of 0.20 g/kg. Mice in each group were orally gavaged once daily for 5 consecutive days. One hour after the final administration, 0.03 ml of xylene was applied to both sides of the right ear of each mouse, while the left ear served as a control. One hour later, the mice were euthanized by cervical dislocation, and 8 mm ear punches were taken from the same location on both ears of each mouse. The ear punches were weighed precisely, and the difference in weight between the right and left ears was calculated as the degree of swelling.

(2) Results

Compared to the model group, all treatment groups were able to suppress xylene-induced ear swelling in mice. Among them, significant differences were observed in groups R, S, T and U compared to the model group. Refer to Table 10 for detailed results.

TABLE 10

Effects of different batches of the traditional Chinese medicine composition on xylene-induced ear swelling in mice ($\overline{X} \pm SD$, n = 10)

| Group name | Degree of ear swelling (g) |
|---|---|
| Model group | 0.0170 ± 0.0059 |
| P | 0.0120 ± 0.0106 |
| Q | 0.0102 ± 0.0063* |
| R | 0.0093 ± 0.0052** |
| S | 0.0089 ± 0.0091** |
| T | 0.092 ± 0.0055** |

TABLE 10-continued

Effects of different batches of the traditional Chinese medicine composition on xylene-induced ear swelling in mice ($\overline{X} \pm SD$, n = 10)

| Group name | Degree of ear swelling (g) |
|---|---|
| U | 0.0090 ± 0.0043** |
| V | 0.0098 ± 0.0040* |
| Positive drug group | 0.0071 ± 0.0038** |

Compared with the model group:
*$P < 0.05$,
**$P < 0.01$.

1.3 Effects of Different Batches of the Traditional Chinese Medicine Composition on Ammonia Solution-Induced Cough in Mice (1) Experimental Method ICR mice weighing between 18-22 g, half male and half female, conducting pre-screening, qualified mice were fed for 3 days, (mice with a latent period of less than 1 minute and experiencing typical coughing at least 3 times within 1 minute are classified as 'coughing' sensitive animals. Otherwise, they are classified as 'non-coughing' and eliminated). Then, randomly divide them into 9 groups: (1) Model group: administered distilled water; (2) Traditional Chinese medicine composition groups P-V: dosage of 4.83 g of crude drug/kg; (3) Positive control group: given a suspension of promethazine hydrochloride, dosage of 1.79 mg/kg. Mice in each group are orally administered once daily for 5 consecutive days. One hour after the final administration, mice are placed in a glass chamber of a multi-function cough and asthma inducer, and 25-28% ammonia solution is sprayed into the chamber for 3 seconds. Subsequently, observe and record the cough latency period and the number of coughs within 3 minutes for each mouse. The criteria for coughing include: abdominal muscle contraction, simultaneous mouth opening, and sometimes coughing sounds."

(2) Results:

Compared to the model group, all treatment groups showed significant prolongation of the cough latency period and/or significant reduction in the number of coughs in mice. Among them, groups of Q, R, S, and U exhibited significant differences compared to the model group, as shown in Table 11.

TABLE 11

Effects of different batches of the traditional Chinese medicine composition on ammonia-induced cough in mice ($\overline{X} \pm SD$, n = 10)

| Group name | Cough latency period (s) | Number of coughs (times) |
|---|---|---|
| Model group | 34.15 ± 6.38 | 19.30 ± 5.77 |
| P | 41.45 ± 8.85 | 16.70 ± 5.68 |
| Q | 42.30 ± 7.17* | 15.40 ± 4.33* |
| R | 47.91 ± 8.96** | 13.10 ± 3.70** |
| S | 47.11 ± 8.79** | 13.20 ± 3.43** |
| T | 41.46 ± 10.54 | 17.00 ± 4.22 |
| U | 48.28 ± 5.96** | 13.50 ± 5.50** |
| V | 40.36 ± 8.88 | 16.70 ± 4.83 |
| Positive drug group | 49.82 ± 8.51** | 13.70 ± 4.52** |

Compared with the model group:
*$P < 0.05$,
**$P < 0.01$.

1.4 the Anti-Novel Coronavirus Efficacy of Various Batches of the Traditional Chinese Medicine Composition (1) Experimental Materials Tested Medicines: Different Batches of the Composition (P-V)

VeroE6 cell: Stored in Pathogen Center, Institute of Medical Laboratory Animal, Chinese Academy of Medical Sciences.

2019-nCoV virus: with titer of 105TCID50/ml, stored at −80 DEG (° C.) in Pathogen Center, Institute of Medical Laboratory Animal, Chinese Academy of Medical Sciences. Viral titer used is 100 TCID50.

(2) Experimental Method

In a sterile 96-well culture plate, 200 ul of a Vero E6 cell with a concentrated of 5×104 cell/ml was added into each well, and was cultured with 5% CO2 for 24 hours at 37 DEG (° C.); a test medicine was diluted to have three concentrations: (1:10000, 1:20000, 1:50000), five wells for each concentration, 100 ul in each well; an equal volume of 100 TCID50 virus was added into each cell, and was incubated for 1 h; 1 h later, cell culture fluid in the 96-well culture plate was discarded, and the medicine mixed liquor was added; cell control, blank control (solvent control) and virus control (negative control) were set at the same time; the cell was incubated in an incubator with 5% CO2 at 37 DEG (° C.) for 4-5 days. Cytopathic effect (CPE) was observed under an optical microscope, complete cell cytopathy was recorded as "++++", 75% cell cytopathy was recorded as "+++", 50% cell cytopathy was recorded as "++", 25% cell cytopathy was recorded as "+", and no cell cytopathy was recorded as (3) Experimental Conditions The Experimental Operations were all completed in a BSL-3 Laboratory.

(4) Result Judgement when the cell had no CPE, the concentration could effectively inhibit the virus; and when the cell had CPE, the concentration was ineffevtive.

(5) Results

The medicine group was set with three concentrations at which 2019-nCoV replication in the cell could be effectively inhibited. The results were shown in Table 12.

TABLE 12

Anti-2019-nCoV effect of 7 batches of the traditional Chinese medicine

| Group name | Concentration | Results |
|---|---|---|
| P | 1:10000 | + |
|   | 1:20000 |   |
|   | 1:50000 |   |
| Q | 1:10000 | + |
|   | 1:20000 |   |
|   | 1:50000 |   |
| R | 1:10000 | − |
|   | 1:20000 |   |
|   | 1:50000 |   |
| S | 1:10000 | − |
|   | 1:20000 |   |
|   | 1:50000 |   |
| T | 1:10000 | + |
|   | 1:20000 |   |
|   | 1:50000 |   |
| U | 1:10000 | − |
|   | 1:20000 |   |
|   | 1:50000 |   |
| V | 1:10000 | + |
|   | 1:20000 |   |
|   | 1:50000 |   |
| Negative control group |   | ++++ |

(6) Conclusion

Based on a cell-level screening result, the composition of R,S,U could inhibit 2019-nCoV replication in the cell at 1:10000, 1:20000, 1:50000 dilution concentration. This indicated that the medicine in the present application had good in-vitro anti-2019-nCoV activity.

CONCLUSION

In three animal models including fever induced by dry yeast in rats, ear swelling induced by xylene in mice, and cough induced by ammonia in mice, overall, groups R, S, and U among the seven different batches of traditional Chinese medicine compositions exhibit better antipyretic, anti-inflammatory, and antitussive effects as well as anti-novel coronavirus effects. Based on the animal experiment, it can be inferred that the therapeutic effects of the traditional Chinese medicine composition can be ensured when containing the said active ingredients in optimal content range. By utilizing the said optimal content range of the active ingredients enables the quality control of the active ingredients in compositions prepared from medicinal materials of different origins and batches, hence ensuring the stable quality and reliable efficacy of traditional Chinese medicine preparations.

The above is merely exemplary illustration of embodiments of the present invention. It should be noted that, for those skilled in the art in this technical field, various modifications and refinements can be made without departing from the principles of the present invention, and these modifications and refinements should also be regarded as within the scope of the present invention.

What is claimed is:

1. A medicine composition, containing active ingredients derived from the following medicines: *Cornu caprae* or *Cornu saigae tataricae, Radix scutellariae Bulbus fritillariae ussuriensis, Radix glycyrrhizae, Radix* et *Rhizoma rhei, Gypsum fibrosum, Calculus bovis* artifactus, and Lapis Chloriti, wherein the active ingredients comprise by weight: 1610.45-1901.21 parts by weight of amino acids, 120.27-167.01 parts by weight of gallic acid, 136.22-172.23 parts by weight of liquiritin, 21.23-37.12 parts by weight of liquiritigenin, 411.30-542.50 parts by weight of baicalin, 40.54-55.01 parts by weight of oroxyloside, 121.11-148.22 parts by weight of wogonoside, 287.88-333.32 parts by weight of glycyrrhizic acid, 12.87-24.11 parts by weight of chrysin-7-O-β-D-glucoronic acid, 50.11-55.21 parts by weight of aloe-emodin 8-O-β-D-glucopyranoside, 30.71-38.56 parts by weight of chrysophanol-1-O-β-D-glucopyranoside, 45.09-57.88 parts by weight of chrysophanol-8-O-β-D-glucopyranoside, 260.11-285.32 parts by weight of hyodeoxycholic acid, 151.11-191.03 parts by weight of cholic acid, wherein said medicine composition is adapted for the treatment of a condition selected from a fever, an inflammatory condition, a cough, or symptoms caused by a coronavirus infection.

2. The medicine composition according to claim 1, wherein the medicine is in any clinically acceptable dosage form.

3. The medicine composition according to claim 2, wherein the dosage form is any one of decoction, granule, capsule, soft capsule, pill, oral liquid, tincture, syrup, suppository, gel, spray and injection.

4. A method for preparing the medicine composition of claim 1, wherein the method comprises the following steps: taking 18.9 parts by weight of *Cornu caprae* or 1.89 parts by weight of *Cornu saigae tataricae,* 9.45 parts u of *Bulbus fritillariae ussuriensis,* 6.3 parts by weight of *Radix* et *Rhizoma rhei,* 3.15 parts by weight of *Radix scutellariae,* 3.15 parts by weight of Lapis Chloriti, 4.724 parts by weight of *Gypsum fibrosum,* 1.89 parts by weight of *Calculus bovis* artifactus and 6.3 parts by weight of *Radix glycyrrhizae*; crushing the *Cornu caprae* or *Cornu saigae tataricae* into fine powder; hydrolyzing the powder with a sodium hydroxide-containing aqueous solution, filtering, and concentrating the filtrate; crushing the Lapis Chloriti and *Gympsum fibrosum* into crude powder; heating and decocting the crushed Lapis Chloriti and *Gympsum fibrosum* in water, filtering, and concentrating the filtrate; extracting the *Calculus bovis* artifactus with ethanol reflux, filtering, and concentrating the filtrate; decocting a rest of medicine in water, filtering, concentrating the filtrate and centrifuging, adding ethanol to the supernatant to precipitate; standing, taking the supernatant, filtering, recovering the ethanol under reduced pressure, concentrating, and combining the concentrated filtrate obtained above.

5. The preparation method according to claim 4, wherein the medicine composition is in the form of an oral liquid, the preparation method comprises:
uniformly mixing the mixed concentrated filtrate with 0.2% steviosin, adding water to make up to 1000 ml, uniformly mixing, boiling for 40 minutes, refrigerating for not less than 48h, filtering, adding water into the filtrate to make up to 1000 ml, adjusting the pH of the filtrate to be 8.0-9.0, filling and sterilizing, wherein *Cornu caprae* 94.5 g or *Cornu saigae tataricae* 9.45 g, *Bulbus fritillariae ussuriensis* 47.25 g, *Radix* et *Rhizoma rhei* 31.50 g, *Radix scutellariae* 15.75 g, Lapis Chloriti 15.75 g, *Gypsum fibrosum* 23.62 g, *Calculus bovis* artifactus 9.45 g and *Radix glycyrrhizae* 31.45 g.

6. A method for treating a condition using the medicine composition according to claim 2, wherein the medicine composition is administered to a subject to treat a condition selected from a fever, an inflammatory condition, a cough, or symptoms caused by a coronavirus infection.

7. A method for detecting the active ingredients of the medicine composition according to claim 1, characterized by conducting HPLC detection, wherein the chromatographic conditions comprise: COSMOSIL-$C_{18}$ chromatographic column with specifications of 4.6 mm×250 mm, 5.0 μm; mobile phase: methanol (B)-aqueous acid (A) (containing 0.1% formic acid), gradient elution: 0-15 min: 10-40% B, 15-70 min: 40-70% B, 70-90 min: 70-100% B; flow rate 0.8-1.2 mL/min, column temperature 30-40° C.

8. A method for making a medicine composition according to claim 1, containing active ingredients derived from the following: *Cornu caprae* or *Cornu saigae tataricae, Radix scutellariae, Bulbus fritillariae ussuriensis, Radix glycyrrhizae, Radix* et *Rhizoma rhei, Gypsum fibrosum, Calculus bovis* artifactus, and Lapis Chloriti, wherein the active ingredients comprise by weight: 1610.45-1901.21 parts by weight of amino acids, 120.27-167.01 parts by weight of gallic acid, 136.22-172.23 parts by weight of liquiritin, 21.23-37.12 parts by weight of liquiritigenin, 411.30-542.50 parts by weight of baicalin, 40.54-55.01 parts by weight of oroxyloside, 121.11-148.22 parts by weight of wogonoside, 287.88-333.32 parts by weight of glycyrrhizic acid, 12.87-24.11 parts by weight of chrysin-7-O-β-D-glucoronic acid, 50.11-55.21 parts by weight of aloe-emodin 8-O-β-D-glucopyranoside, 30.71-38.56 parts by weight of chrysophanol-1-O-β-D-glucopyranoside, 45.09-57.88 parts by weight of chrysophanol-8-O-β-D-glucopyranoside, 260.11-285.32 parts by weight of hyodeoxycholic acid, 151.11-191.03 parts by weight of cholic acid;

wherein the method comprises the following steps:
taking 18.9 parts by weight of *Cornu caprae* or 1.89 parts by weight of *Cornu saigae tataricae,* 9.45 parts u of *Bulbus fritillariae ussuriensis,* 6.3 parts by weight of *Radix* et *Rhizoma rhei,* 3.15 parts by weight of *Radix scutellariae,* 3.15 parts by weight of Lapis Chloriti, 4.724 parts by weight of *Gypsum fibrosum,* 1.89 parts by weight of *Calculus bovis* artifactus and 6.3 parts by weight of *Radix glycyrrhizae;*
crushing the *Cornu caprae* or *Cornu saigae tataricae* into fine powder;
hydrolyzing the powder with a sodium hydroxide-containing aqueous solution, filtering, and concentrating the filtrate;
crushing the Lapis Chloriti and *Gympsum fibrosum* into crude powder;
heating and decocting the crushed Lapis Chloriti and *Gympsum fibrosum* in water, filtering, and concentrating the filtrate;
extracting the *Calculus bovis* artifactus with ethanol reflux, filtering, and concentrating the filtrate;
decocting a rest of medicine in water, filtering, concentrating the filtrate and centrifuging, adding ethanol to the supernatant to precipitate; standing, taking the supernatant, filtering, recovering the ethanol under reduced pressure, concentrating, and combining the concentrated filtrate obtained above.

9. A method for treating antipyretic, inflammatory, antitussive and/or anti-novel coronavirus; wherein the method comprising:

(a) Preparing a traditional Chinese medicine composition, comprising the following steps:

taking 18.9 parts by weight of *Cornu caprae* or 1.89 parts by weight of *Cornu saigae tataricae,* 9.45 parts u of *Bulbus fritillariae ussuriensis,* 6.3 parts by weight of *Radix et Rhizoma rhei,* 3.15 parts by weight of *Radix scutellariae,* 3.15 parts by weight of Lapis Chloriti, 4.724 parts by weight of *Gypsum fibrosum,* 1.89 parts by weight of *Calculus bovis* artifactus and 6.3 parts by weight of *Radix glycyrrhizae;* crushing the *Cornu caprae* or *Cornu saigae tataricae* into fine powder;

hydrolyzing the powder with a sodium hydroxide-containing aqueous solution, filtering, and concentrating the filtrate;

crushing the Lapis Chloriti and *Gympsum fibrosum* into crude powder;

heating and decocting the crushed Lapis Chloriti and *Gympsum fibrosum* in water, filtering, and concentrating the filtrate;

extracting the *Calculus bovis* artifactus with ethanol reflux, filtering, and concentrating the filtrate;

decocting a rest of medicine in water, filtering, concentrating the filtrate and centrifuging, adding ethanol to the supernatant to precipitate; standing, taking the supernatant, filtering, recovering the ethanol under reduced pressure, concentrating, and combining the concentrated filtrate obtained above;

(b) Detecting the active ingredients of the traditional Chinese medicine composition by conducting HPLC detection, wherein the chromatographic conditions comprise: COSMOSIL-$C_{18}$ chromatographic column with specifications of 4.6 mm×250 mm, 5.0 um; mobile phase: methanol (B)-aqueous acid (A) (containing 0.1% formic acid), gradient elution: 0-15 min: 10-40% B, 15-70 min: 40-70% B, 70-90 min: 70-100% B; flow rate 0.8-1.2 mL/min, column temperature 30-40° C.;

(c) Administrating the traditional Chinese medicine composition, when the detecting result of the active ingredients of the traditional Chinese medicine composition fall within the following: the active ingredients comprise by weight: 1610.45-1901.21 parts by weight of amino acids, 120.27-167.01 parts by weight of gallic acid, 136.22-172.23 parts by weight of liquiritin, 21.23-37.12 parts by weight of liquiritigenin, 411.30-542.50 parts by weight of baicalin, 40.54-55.01 parts by weight of oroxyloside, 121.11-148.22 parts by weight of wogonoside, 287.88-333.32 parts by weight of glycyrrhizic acid, 12.87-24.11 parts by weight of chrysin-7-O-β-D-glucoronic acid, 50.11-55.21 parts by weight of aloe-emodin 8-O-β-D-glucopyranoside, 30.71-38.56 parts by weight of chrysophanol-1-O-β-D-glucopyranoside, 45.09-57.88 parts by weight of chrysophanol-8-O-β-D-glucopyranoside, 260.11-285.32 parts by weight of hyodeoxycholic acid, 151.11-191.03 parts by weight of cholic acid.

\* \* \* \* \*